United States Patent [19]

Malek et al.

[11] Patent Number: 5,380,928

[45] Date of Patent: Jan. 10, 1995

[54] TWO STEP OXIDATION PROCESS FOR THE PRODUCTION OF CARBOXYLIC ACIDS SUCH AS AZELAIC ACID FROM UNSATURATED SUBSTRATES

[75] Inventors: Abdul Malek, Brossard; Clevys J. Monasterios, Montreal; G. Ronald Brown, Dollard des Ormeaux; Ved P. Gupta, Lasalle, all of Canada

[73] Assignee: Synergistics Industries, Inc., Canada

[21] Appl. No.: 107,979

[22] Filed: Aug. 18, 1993

[51] Int. Cl.$^6$ .............................................. E07C 55/00
[52] U.S. Cl. .................................. 562/512.4; 562/524
[58] Field of Search .............................. 562/512.4, 524

[56] References Cited

U.S. PATENT DOCUMENTS

| | | | |
|---|---|---|---|
| 2,136,144 | 11/1938 | Milas et al. | 562/512.4 |
| 2,323,861 | 7/1943 | Zellner | 562/512.4 |
| 2,682,553 | 6/1954 | Kirk et al. | 562/524 X |
| 2,791,598 | 5/1957 | Brown et al. | 562/512.4 |
| 2,824,134 | 2/1958 | Hill et al. | 562/512.4 X |
| 2,918,487 | 12/1959 | Patterson et al. | 562/512.4 X |
| 2,978,473 | 4/1961 | Chafetz et al. | 562/512.4 |
| 3,388,157 | 6/1968 | Barona | 562/512.4 |
| 3,948,983 | 4/1976 | Hackmann et al. | 562/548 |
| 4,172,086 | 10/1979 | Berkowitz | 562/512.4 |
| 4,328,265 | 5/1982 | Slinkard et al. | 562/512.2 |

FOREIGN PATENT DOCUMENTS

3016225A1 10/1981 Germany.

OTHER PUBLICATIONS

Encyclopedia of Chemical Technology, 3rd Ed., vol. 7, 1978, pp. 620–621.
Ogata, "Oxidations with Nitric Acid or Nitrogen Oxides", Oxidation in Organic Chemistry, Part C, vol. 5, 1978, pp.295–317.
Swern, "Chemical Oxidation", Fatty Acids, Second Edition, Part 2, Chapter XIII, 1961, pp. 1307–1353.
Seymour, "Adipic Acid", Encyclopedia of Chemical Processing & Design, vol. 2, pp. 128–146, 1968.

*Primary Examiner*—Arthur C. Prescott
*Attorney, Agent, or Firm*—Larson and Taylor

[57] ABSTRACT

The invention relates to a method for the high yield production of dicarboxylic acids such as azelaic acid by the controlled two step oxidation of an unsaturated hydrocarbon substrate. The method consists of two steps and involves the derivatization of the unsaturated substrate which locks and directs oxidative cleavage at the site of unsaturation to yield the desired acids.

23 Claims, No Drawings

TWO STEP OXIDATION PROCESS FOR THE PRODUCTION OF CARBOXYLIC ACIDS SUCH AS AZELAIC ACID FROM UNSATURATED SUBSTRATES

FIELD OF THE INVENTION

The invention relates to a method for the production in high yield of dicarboxylic acids such as azelaic acid, by the controlled two step oxidation of an unsaturated hydrocarbon substrate. The process comprises a derivatization of the substrate, preferably with a peroxy organic acid, followed by oxidative cleavage of the derivatized substrate into a carboxylic acid, preferably with an oxidizing acid such as nitric acid in the presence of a vanadium catalyst.

BACKGROUND OF THE INVENTION

Commercially available dicarboxylic acids are obtained through a limited number of processes which are well known to those skilled in the art. Hence, carboxylic acids are generally produced through oxidation of saturated or unsaturated hydrocarbon substrates such as fatty acid substrates using either a gaseous component such as air and ozone, a nitric acid/metal catalyst component or a combination of both components. Numerous prior art documents disclose variants of such oxidation processes.

In the case of carboxylic acid production using air, British Patent 809,452 assigned to Celanese Corporation of America describes a process for the preparation mono and diacarboxylic acids. The process comprises the air conversion of a mixture of hydroxy fatty acids having up to 10% by weight concentration in its unsaturated counterpart. Also, U.S. Pat. No. 2,813,113 granted to Emery Industries describes the production of azelaic acid from unsaturated fatty acids having 10 to 24 carbon atoms. The process consists in a two-step ozone-air oxidation of straight chain unsaturated fatty acids such as oleic acid. Ozone as an oxidant is highly reactive, selective and gives rise to relatively clean reaction products with minimal residues or by-products. Nevertheless, ozone production requires high technology equipment, large capital investments with great annuity costs. Its concentration (1.5-2% ozone by weight) implies a large volume of gases to be processed that negatively influences the oxidation kinetics, requires high costs and strict safety control.

A number of prior art documents describe variants of air-oxidation processes. For example, U.S. Pat. No. 4,328,365 discloses a process for the oxidation of hydrocarbons using a carbon monoxide-reduced vanadium pentoxide catalyst immobilized on an inert support. U.S. Pat. No. 2,136,144 describes a process for the conversion of cycloalkenes to acids using oxygen and a vanadium catalyst. Also, U.S. Pat. No. 3,388,157 describes a process for the air oxidation of alkanes. This process, which appears to involve the use of high temperatures, requires elaborated separation systems using distillation and oxidation.

Oxidation of fats and fatty acids with nitric acid and oxides of nitrogen is one of the oldest reactions in chemistry. Nitric acid is an inexpensive strong oxidant. It has however only been used commercially to a limited extent because of the non-specificity of the resulting reaction products and the difficulty in controlling the reaction.

Oxidation of unsaturated fatty acids with nitric acid is more specific than the oxidation of saturated fatty acids but it still generates a mixture of dibasic acids. For example, oxidation of oleic acid with 85-95% $HNO_3$ at 20°-25° C. for 3-8 hours gives 44-56% azelaic acid, 16-17% suberic acid, 7-12% pimelic acid, 6-10% succinic and glutaric acid, 3-4% adipic acid and 0-2% sebacic acid. Oxidation of conjugated linoleic acid and tall oil fatty acids gives an even wider distribution of dibasic acids and total lower yields than with pure substrates and the reaction is extremely slow.

Still, many prior art references describe methods for producing dicarboxylic acids which are essentially one-step methods for oxidizing aliphatic or aromatic substrates using a strong acid such as nitric acid in the presence or absence of a vanadium catalyst. Hence, in U.S. Pat. No. 2,323,861, a process is described for converting unsaturated hydrocarbons such as cyclohexenes to dibasic acids by reacting the cyclohehexene substrate with nitric acid and a variety of catalysts including ammonium vanadate. Also, one step reaction of 88% nitric acid and 0.1% ammonium metavanadate catalyst on unsaturated substrates has been reported in U.S. Pat. No. 2,203,680. However, the reaction conditions were such that it took two days at room temperature to obtain 50% diacid products.

In U.S. Pat. No. 2,343,534 assigned to du Pont, there is described a process for the industrial production of adipic acid. In this process, a cyclohexane/cyclohexanol combination is reacted in the presence of nitric acid and an ammonium metavanadate/copper nitrate catalyst mixture. Also, azelaic acid and other diacids and monoacids have been prepared by direct action of chromic acid and sulphuric acid on oleic acid as described in U.S. Pat. No. 2,450,858. Also, in German Patent 3,016,225, there is described an oxidative post-treatment for purifying di or polybasic carboxylic acids. The acids are initially produced by reacting unsaturated hydrocarbons with nitric acid.

The combined use of air and acid/catalyst components has also been reported in the literature. In U.S. Pat. No. 1,991,188, phthalic acid is produced by treating either o-xylene or naphthalene with nitric acid in the presence of oxygen gas and vanadium pentoxide. U.S. Pat. No. 2,662,908 refers to the treatment of 24 carbon atom fatty acids with air in the presence of dilute nitric acid (8-30%) at high temperature.

Oxidation processes involving both air and nitric acid are also described in U.S. Pat. No. 2,791,598. The document discloses a process by which saturated aliphatic hydrocarbons are converted to organic acids by oxidizing the saturated aliphatic hydrocarbon substrates with air or other oxygen-containing gases and nitric acid. A catalyst such as vanadium pentoxide can also be used. In U.S. Pat. No. 2,978,473, a process is described to prepare dibasic acids from hydrocarbon substrates. In this process, the hydrocarbon substrate is oxidized with air in the presence of a metal catalyst and submitted to water extraction and separation prior to reaction with nitric acid. This process appears to be complex and requires many purification steps.

In one-step oxidation reactions using either a nitric acid/catalyst component, a gaseous component or a combination of both, the major drawbacks are random attack on the substrate and rearrangement reactions which give rise to low yields of a mixture of dibasic acids. Furthermore, impurities substantially lower the yield of the desired final products. Also, direct action of nitric acid on unsaturated substrates leads to the formation of nitroso and nitrate compounds. These reactions compete with the oxidation reaction, which lowers the yield of the diacid products as well as producing a multi-component mixture.

In summary, current oxidation processes for the production of diabasic acids from hydrocarbon substrates suffer from low yields because the reaction usually lacks specificity and does not discriminate from one possible oxidation site to another. There appears to be a need for improved processes allowing a more efficient targetting of the desired oxidation site in the substrate.

SUMMARY OF THE INVENTION

In accordance with the present invention, there is provided a process for the preparation of carboxylic acids by the oxidative cleavage of a substrate comprising a hydrocarbon having at least one double bond. The process comprises locking and directing the oxidative cleavage of the hydrocarbon at the double bond by conducting a derivatization of the hydrocarbon at the double bond to convert the hydrocarbon into its corresponding hydroxy acyloxy derivative. The resulting hydroxy acyloxy derivative has a hydroxy acyloxy moiety at the site of the double bond. The resulting derivative thus obtained is then oxidized into a carboxylic acid, for example, by cleaving the hydroxy acyloxy derivative at its hydroxy acyloxy moiety and the desired carboxylic acid is recovered.

Preferably, the hydrocarbon is derivatized through selective conversion of the unsaturated moiety thereon by being reacted with a peroxy acid to yield the corresponding hydroxy acyloxy derivative. The hydroxy acyloxy derivative is then oxidized into the desired carboxylic acid by being preferably reacted with an acid such as nitric acid or with an oxide of nitrogen. A catalyst, preferably a metal catalyst and most preferably a transition metal catalyst, is used to enhance the reaction with nitric acid.

The method is particularly useful for the oxidation of fatty acid rich substrates into mono and dicarboxylic acids such as azelaic acid produced from $C_{18}$ unsaturated fatty acid substrates and their triglycerides. Thus, the invention also specifically relates to a process for the preparation of azelaic acid. The process comprises reacting a fatty acid substrate comprising oleic, linoleic and linolenic acid components with a peroxy organic acid to yield mono-, di- and tri-hydroxy acyloxy derivatized acids from the oleic, linoleic and linolenic acid components. The derivatized acids are then oxidized to yield a mixture of mono- and dibasic carboxylic acids comprising at least one acid selected from azelaic acid, suberic acid, hexanoic acid, octanoic acid and pelargonic acid. The resulting acids are then recovered from the mixture.

The two-step process adds an initial step of derivatization of the double bond of the substrate prior to the oxidative cleavage of the resulting derivative. This double bond derivatization fixes the position at which oxidation occurs. It has the effect of providing higher yields of the desired final product by directing the reaction toward the derivatized site, thereby decreasing the likelihood of random attack on the substrate. One of the important aspects of the invention therefore resides in the combination of steps that efficiently lock and direct the cleavage of the hydrocarbon substrate at the site of unsaturation. This is a progressive oxidation pathway where the substrate is derivatized previous to its cleavage into the corresponding carboxylic acids. The conversion of the unsaturated moiety on the hydrocarbon substrate into a hydroxy acyloxy group increases the scope of the fatty acid sources available as oxidation substrates. For example, the yields and composition of the dicarboxylic acid reaction products is essentially the same whether tall oil fatty acids (TOFA), canola oil fatty acids (COFA) or oleic acid among others are used as a substrate.

Furthermore, conversion of the unsaturated moiety of the hydrocarbon substrate into a hydroxy acyloxy functionality precludes the formation of nitroso and nitrate derivatives which decrease the yield of the reaction products. When the double bond of the substrate has been previously derivatized, nitric acid and its oxides react as oxidizing agents exclusively. Their actions are then directed to the former unsaturation site on the hydrocarbon substrate that has been converted to its corresponding hydroxy acyloxy derivative.

DETAILED DESCRIPTION OF THE INVENTION

The present invention relates to a process for the production of mono- and dicarboxylic acids such as hexanoic, pelargonic, azelaic and suberic acids, from unsaturated substrates. This is a two-step process that comprises the non-catalytic derivatization of an unsaturated substrate followed by a catalytic oxidative cleavage of the derivatized substrate into its corresponding carboxylic acids. The reactants involved in each step of the process together with the appropriate reaction conditions are described in further detail hereinbelow.

Step 1: derivatization of the substrate

In the first step of the process of the present invention, the unsaturated substrate undergoes a derivatization at the unsaturated site. This non-catalytic derivatization is preferably conducted through treatment of the unsaturated substrate with a peroxy organic acid to yield the corresponding hydroxy acyloxy derivative.

a) Reactants

1° Substrate

Generally speaking, the substrate can be chosen from a wide variety of unsaturated fatty acid substrates. It is important that the substrate contain a proportion of unsaturated hydrocarbons that can be selectively oxidized at their sites of unsaturation. Preferably, the substrates can be selected from by-products of paper manufacturing processes or oils from agricultural sources. It is most preferred that the substrate have more than 90% unsaturated fatty acid content.

Among specific fatty acid substrates that are contemplated for use in the context in the present invention, fatty acid rich substrates including mono-, di- and tri-unsaturated fatty acids, and hydroxylated acids of natural and synthetic sources as well as their triglycerides, products and derivatives are included. Preferred are those unsaturated substrates having between 16 and 22 carbon atoms, with unsaturated $C_{18}$ fatty acid rich substrates containing at least 90% of oleic, linoleic and linolenic acids being most preferred. Other examples include $C_{16}$–$C_{22}$ substrates containing unsaturated $C_{16}$–$C_{22}$ hydrocarbons such as palmitoleic acid, oleic acid, linoleic acid, linolenic acid and ricinoleic acid, tall, rapeseed, canola, olive and castor oils, canola oil fatty acids (COFA), tall oil fatty acids (TOFA), rapeseed oil fatty acids (ROFA), vegetable oil fatty acids (VOFA) and other triglycerides.

It is important to mention that the use of a good quality substrate, that is a substrate having a relatively high percentage of unsaturated fatty acids, substantially enhances the overall yield of the process.

2° Peroxy organic acid

The use of appropriate peroxy acids to produce the desired hydroxy acyloxy derivative is particularly indicated in the context of the present invention because peroxy acids react directly with the double bond functionality on the unsaturated substrate.

The reaction of peroxy organic acids on mono unsaturated fatty acids mainly produces oxirane (α-epoxy) derivatives. Fatty acid epoxides are used as lubricants and plasticizers. Some epoxides are useful in polymerization reactions because of the reactivity of the three member ring. Epoxides are mainly prepared as intermediates in glycol formation reactions. Once the ring is formed, the choice of hydrolysis reagent directs the orientation of the hydroxy groups. Glycol derivatives of fatty acid epoxides can be obtained by either acidic or basic hydrolysis of the oxirane ring. Peroxy benzoic acid is one of the most common epoxidizing agent as peroxy benzoic acid reactions always produce an epoxide ring. Hydrolysis is necessary to obtain the desired derivatives.

In the context of the present invention, it is preferred to use peroxy acids which, upon reaction with an unsaturated hydrocarbon substrate under suitable reaction conditions, directly produce the desired hydroxy acyloxy derivative. In this regard, peroxy acids obtained from lower carboxylic acids, such as peroxy formic acid, peroxy acetic acid, peroxy propionic acid and the like are most preferred. Peroxy acetic acid reactions generate oxirane rings if inert solvents are used and the reaction is not catalyzed by the presence of a strong acid. However, other reaction conditions lead directly to the formation of the hydroxy acetoxy derivative. In the case of peroxy formic acid, reactions with unsaturated substrates do not produce oxirane rings. Once the oxirane ring is formed, it readily reacts with the formic acid present to form a hydroxy formoxy derivative.

Peroxy organic acids are prepared by the reaction of hydrogen peroxide with carboxylic acids, anhydrides and acid chlorides. Preferably, the peroxy organic acids are generated in a separate operation or in situ by the reaction of a carboxylic acid with a 30–90% by weight hydrogen peroxide solution. Alternatively, the peroxy carboxylic acids can be produced by reacting an aromatic or aliphatic organic acid with an excess of hydrogen peroxide in the presence of a suitable strong acid catalyst. A process of this type is described in U.S. Pat. No. 4,172,086, which hereby incorporated by reference.

b) Reaction conditions

The reaction temperature and pressure are so chosen to minimize oxygen losses by the thermal decomposition of the reactive peroxide. A reaction temperature of 40° C. at atmospheric pressure is common but temperatures ranging from 25° C. to 60° C. and pressures ranging from 1 to 5 atmospheres can be contemplated.

By this treatment, the unsaturated hydrocarbon is derivatized into its corresponding hydroxy acyloxy derivative at the double bond. It therefore locks and selectively directs the subsequent cleavage of the fatty acid substrate at the unsaturation site.

Hydroxy acyloxy derivatives can be prepared from the variety of unsaturated fatty acids referred to previously. Mixtures of acids and acids from different sources such as tall oil and canola oil can be used without substantially affecting the yield or composition of the final diacid reaction product. Furthermore, once the hydroxy acyloxy derivative has been prepared, it can be subjected to further chemical treatment without modification or purifications procedures.

Step-two: Oxidation of the derived substrate

In the second step of the process of the present invention, the hydroxy acyloxy derivative obtained in step 1 is cleaved into its corresponding mono- and dicarboxylic acid.

a) Oxidants

The preferred reactants to be used as oxidants for the conversion of the hydroxy acyloxy derivative include oxidizing acids. Most preferred is nitric acid in concentrations that can range from 30–70% by weight. A catalyst must be used together with nitric acid. Preferred metal catalyst include transition metal catalysts, with the most preferred catalyst being a vanadium catalyst selected from ammonium metavanadate, sodium metavanadate and vanadium pentoxide. Optionally, the vanadium catalyst can also be combined with a co-catalyst such as metallic copper, copper nitrate, copper sulphate as well as other transition metal salts or oxides. The concentration of the vanadium catalyst can range from 0–5% by weight of substrate.

b) Reaction conditions

A reaction temperature ranging between 65° and 70° C. is very common but a lower range of 30°–40° C. or a higher range of 80°–85° C. or any temperature between 30° and 85° C. can be chosen depending on the substrate used. The pressure of the reaction and its duration are also variable parameters that reflect the desired product and the substrate used. The resulting product varies depending on the substrate but can for example be a mixture of mono- and dicarboxylic acids selected from hexanoic, pelargonic, azelaic and suberic acids. As mentioned previously, catalytic oxidation on hydroxy acyloxy fatty acid derivatives produces dibasic acid products in good yields, usually with small amounts of lower dibasic acid impurities. Derivatization locks and directs oxidative cleavage to a specific site, thus eliminating random attack on the aliphatic chain.

The following examples are provided to illustrate rather than limit the scope of the present invention.

EXAMPLE 1

Two step oxidation of tall oil fatty acid using peroxyformic acid and nitric acid/sodium metavanadate.

Step 1 (derivatization of the double bond):

A hydroxy acyloxy derivative of tall oil fatty acid (TOFA) was prepared by mixing 200 g of TOFA (63% oleic acid, 31% linoleic acid) with 500 mL of formic acid. The resulting mixture was vigorously stirred by magnetic action. Hydrogen peroxide solution, 180 mL of 35% by weight, was added in aliquots to the mixture throughout the course of the reaction. A third of the total amount of peroxide solution was added at once to initiate the reaction. The peroxyformic acid in this case was prepared in situ.

The start of the reaction was signalled by heat evolution and a dramatic color change, from pale yellow to deep rust red. The exothermicity of the reaction required external cooling to control the temperature. The reaction was maintained at 40° C. to minimize oxygen loss through the decomposition of the peroxide. As required, the temperature of the reaction was maintained with an external heating source. A total reaction time of 5 to 6 hours was necessary for complete reaction. The end of the reaction was indicated by a color change; the reaction mixture changed from rust red back to yellow. One last aliquot of peroxide solution was added at the end of the reaction period to provide a peroxide atmosphere during the reaction work-up. TOFA as a substrate produced a mixture of mono- and dihydroxy formoxy stearic acid from the oleic and linoleic acid components, respectively. The final product was obtained in essentially 100% yield by removing the unreacted formic acid and hydrogen peroxide as well as water. It was obtained as a viscous, syrupy yellow oil that upon gas chromatographic analysis of the methyl esters of the reaction mixture gave no evidence of unreacted substrate.

Step 2 (oxidation of derivative obtained from step 1):

A 2 L-three neck flask fitted with an air condenser attached to a gas scrubbing apparatus was filled with 500 mL of concentrated nitric acid (70% by weight). The acid was stirred by magnetic action and 1 g of sodium metavanadate was added to it. The resulting mixture was heated slowly to 40°–50° C. At this point a small amount of product as obtained from Step 1 was added to the acid-catalyst mixture. Heating was continued until a sharp temperature increase accompanied by evolution of $NO_x$ gases was observed. The reaction temperature was self-sustained with the addition of aliquots of the hydroxy formoxy ester mixture obtained from Step 1. (External cooling may be required throughout the substrate addition period to keep the temperature within 65°–70° C.). At the end of the addition period the reaction temperature was maintained for an additional 1.5 to 2 hours, for a total reaction time of 3 hours.

The final products were obtained by quenching the reaction by adding excess water and extracting the organic layer with purified diethyl ether. The ether extract was dried over anhydrous sodium sulfate overnight before its removal with a roto-vap apparatus. Addition of petroleum ether (boiling range 35°–60° C.) to the product mixture caused precipitation of the di-acid component. Vacuum filtration was used to remove the solid diacids from the liquid monoacid mixture. The latter was obtained by removing the excess petroleum ether from the resulting filtrate. Quantitative analysis by gas chromatography of the methyl esters showed that the products to be 96% yield of diacid (66% azelaic, 30% suberic) and 60% monobasic acid product (30% hexanoic, 10% octanoic and 20% pelargonic) on average. (Yields are based on theoretical fatty acid content).

EXAMPLE 2

Two step oxidation of Canola oil fatty acid using peroxyformic acid and nitric acid/sodium metavanadate.

Step 1 (derivatization of the double bond):

The procedure followed in step 1 of Example 1 was used but canola oil fatty acid (COFA) replaced TOFA as a substrate. The fatty acid composition was 60% oleic acid, 25% linoleic acid and 8% linolenic acid. The start of the reaction was signalled by heat evolution only, no color change was observed. The initial yellow color of the reaction mixture faded throughout the course of the reaction. At the end of the reaction period, the reaction product was completely white. COFA as a substrate produced a mixture of mono-, di- and trihydroxy formoxy stearic acid from oleic, linoleic and linolenic acid components, respectively. The final product was a soft white substance. Gas chromatographic analysis of the methyl esters of the reaction mixture showed absence of starting material.

Step 2 (oxidation of the derivative obtained from Step 1):

The procedure followed in step 2 of Example 1 was used but the reaction was carried out with the hydroxy formoxy stearic acid mixture produced as described in Step 1 of Example 2. At the end of the addition period the reaction temperature (65°–70° C.) was maintained for an extra 3.5 to 4 hours to a total reaction time of 4.5 to 5 hours. Cleavage of hydroxy acyloxy derivatives of COFA or pure oleic acid required twice the reaction time of TOFA derivatives. The final product was a mixture of mono- and dicarboxylic acids in yield and composition similar to that described in Example 1, Step 2.

EXAMPLE 3

Two step oxidation of tall oil fatty acid using peroxyacetic acid and nitric acid/sodium metavanadate.

Step 1 (derivatization of the double bond):

As described in Example 1, Step 1, a reaction was carried out by placing 100 g of TOFA in a reaction vessel with 200 mL of glacial acetic acid and 4 g of concentrated sulfuric acid. Hydrogen peroxide solution, 100 mL of 30% by weight, was added throughout the course of the reaction. The reaction was allowed to proceed for a 4 hour period. Removal of the excess reactants yielded a mixture of mono- and dihydroxy acetoxy stearic acid from the oleic and linoleic acid components in TOFA, respectively. Gas chromatographic analysis of the methyl esters of the reaction mixture showed no evidence of unreacted substrate.

Step 2 (oxidation of the derivative obtained from Step 1):

The procedure followed in Step 2 of Example 1 was used except that the reaction was carried out with the hydroxy acetoxy stearic acid mixture obtained in Step 1 of Example 3. The oxidative cleavage of the hydroxy acetoxy ester derivatives from TOFA were not different from the reaction with the hydroxy formoxy ester counterpart. Reaction conditions, composition and yield of products were comparable to that cited in Example 1, Step 2.

EXAMPLE 4

Two step oxidation of oleic acid using peroxyformic acid and nitric acid/vanadium pentoxide.

Step 1 (derivatization of the double bond):

The reaction was carried out in the manner of Example 1, Step 1 with the exception that 10 g of laboratory grade oleic acid were used as the substrate. The reactant peroxyformic acid was prepared in situ by mixing 30 mL of formic acid with 20 mL of 30% by weight hydrogen peroxide solution. Oleic acid as a substrate produced monohydroxy formoxy stearic acid only. The product was a white, hard substance. Gas chromatographic analysis showed the absence of starting material (oleic acid).

Step 2 (oxidation of the derivative obtained from Step 1):

As in Example 1, Step 2 the reaction was carried out by adding 30 mL of concentrated nitric acid and 0.05 g of vanadium pentoxide to the hydroxy formoxy stearic acid product as obtained by the procedure described in Step 1 of Example 4. The resulting mixture was heated slowly until a sharp temperature increase accompanied by a strong evolution of $NO_x$ gas was observed. In some cases, external cooling was required to keep the reaction temperature between 65°–70 °C. The reaction was allowed to take place for a period of 3.5–4 hours. The reaction products consisted of a mixture of carboxylic acids including pelargonic and octanoic acids, the former being the major monobasic acid component. A 96% yield of azelaic and suberic acids in a 80:20 ratio, respectively, was obtained.

Reaction parameters such as acid concentration, duration, temperature and so on can affect the yield and composition of the reaction products. For example, suberic acid ($C_8$ dicarboxylic acid) is produced in small amounts along with azelaic acid in the two step process of the invention. During the course of the work that led to the invention, it was observed that:

Under the same reaction conditions of amount of substrate, nitric acid and catalyst, production of suberic acid follows the sequence:

linoleic acid > TOFA > COFA > oleic acid.

The oxidative cleavage of the hydroxy acyloxy derivative of TOFA takes half the time of those of COFA, oleic acid and linoleic acid (2 h. v. 4 h.) respectively. It is believed that the rosin acids, unsaponifiables and inorganic salts present in TOFA have a catalytic effect on the reaction.

small scale reactions (ten grams quantities) using the hydroxy formoxy derivative of oleic acid produced azelaic acid only. Reactions carried out with scale up quantities generated suberic acid as a by-product. Reaction conditions such as duration and amount of substrate reacted at any one time can be modified to suit the handling of larger quantities and to meet safety requirements. Such modifications, small as they are, can have a significant effect on the composition of the final products.

The azelaic/suberic acid ratio obtained by the oxidative cleavage of the hydroxy formoxy derivative of TOFA is independent of the amount of catalyst (0.5%, 0.25%) or the concentration of nitric acid used (69%, 50%). Conversely, the yield and purity of the reaction product is significantly affected.

We claim:

1. A process for the preparation of carboxylic acids by the oxidative cleavage of a substrate comprising a hydrocarbon bearing at least one double bond, said process comprising:
locking and directing the oxidative cleavage of said hydrocarbon at the site of said double bond by conducting a derivatization of said hydrocarbon at said double bond to convert said hydrocarbon into its corresponding hydroxy acyloxy derivative, said resulting derivative having a hydroxy acyloxy moiety at the site of said double bond;
oxidizing said hydroxy acyloxy derivative into a carboxylic acid by cleaving said hydroxy acyloxy derivative at said hydroxy acyloxy moiety; and recovering the desired carboxylic acid.

2. A process according to claim 1 wherein said hydrocarbon is modified through selective derivatization of the double bond thereon by being reacted with a peroxy organic acid to yield a hydroxy acyloxy derivative.

3. A process according to claim 1 wherein said hydroxy acyloxy derivative is oxidized into its corresponding carboxylic acid by being reacted with nitric acid or an oxide of nitrogen in the presence of a transition metal catalyst.

4. A process according to claim 3 wherein said transition metal catalyst is a vanadium catalyst selected from ammonium metavanadate, sodium metavanadate and vanadium pentoxide.

5. A process according to claim 3 wherein said transition metal catalyst is coupled with a co-catalyst selected from the group consisting of metallic copper, copper nitrate and copper sulfate.

6. A process according to claim 1 wherein said hydrocarbon is selected from unsaturated $C_{16}$–$C_{22}$ hydrocarbons.

7. A process according to claim 1 wherein said unsaturated hydrocarbon is derivatized into its corresponding hydroxy acyloxy derivative by being reacted with a peroxy organic acid at a temperature ranging from 25°–60° C. and an air pressure ranging from 1–5 atmospheres.

8. A process according to claim 2 wherein said peroxy organic acid is a $C_1$–$C_4$ acid.

9. A process according to claim 1, wherein said hydroxy acyloxy derivative is oxidized into its corresponding carboxylic acid by being reacted with nitric acid or oxides of nitrogen in the presence of a vanadium catalyst at a temperature ranging between 30° and 85° C.

10. A process according to claim 3 wherein said nitric acid concentration ranges from 30–70% by weight.

11. A process according to claim 4 wherein said vanadium catalyst is present in concentrations of 5% by weight of substrate or less.

12. A process according to claim 1, wherein said substrate is selected from the group consisting of palmitoleic acid, oleic acid, linoleic acid, linolenic acid, ricinoleic acid, tall oil, rapeseed oil, canola oil, olive oil, castor oil or mixtures thereof, canola oil fatty acids, tall oil fatty acids, rapeseed oil fatty acids and vegetable oil fatty acids.

13. A process for the preparation of azelaic acid, said process comprising:
reacting a fatty acid substrate comprising oleic linoleic and linolenic acid components with a peroxy organic acid to yield mono-, di- and trihydroxy acyloxy derivatives from oleic, linoleic and linolenic acid components;
oxidizing said derivatives to yield a mixture of mono- and dibasic carboxylic acids comprising at least one acid selected from azelaic acid, suberic acid, hexanoic acid, octanoic acid and pelargonic acid; and recovering azelaic acid from said mixture.

14. A process according to claim 13, wherein said fatty acid substrate is selected from the group consisting of tall oil fatty acid and canola oil fatty acid.

15. A process according to claim 13, wherein said tall oil fatty acid comprises 63% oleic acid and 31% linoleic acid.

16. A process according to claim 13, wherein said canola oil fatty acid comprises 60% oleic acid, 25% linoleic acid and 8% linolenic acid.

17. A process according to claim 13, wherein said peroxy organic acid is peroxyformic acid.

18. A process according to claim 13, wherein said fatty acid substrate is reacted with said peroxy organic acid at a temperature of about 40° C.

19. A process according to claim 13, wherein said derivatives are oxidized by being reacted with nitric acid.

20. A process according to claim 13, wherein said derivatives are oxidized by being reacted with nitric acid in the presence of a vanadium catalyst.

21. A process according to claim 20, wherein said vanadium catalyst is sodium metavanadate.

22. A process according to claim 20, wherein the concentration of nitric acid is about 70% by weight.

23. A process according to claim 13 wherein said oxidation of said derivatives is carried out at a temperature ranging from about 65° C. to about 70° C. for a period of time ranging from about 2 hours to about 4 hours.

* * * * *